United States Patent [19]

Dosmann

[11] Patent Number: 4,930,865
[45] Date of Patent: Jun. 5, 1990

[54] OPTICAL TRANSMISSION SPECTROMETER

[75] Inventor: Andres J. Dosmann, Mishawaka, Ind.

[73] Assignee: Miles Inc., Elkhart, Ind.

[21] Appl. No.: 267,309

[22] Filed: Nov. 4, 1988

[51] Int. Cl.$^5$ .................. G02B 27/12; G02B 5/04; G01J 3/28

[52] U.S. Cl. .................. 350/169; 350/286; 356/326

[58] Field of Search .............. 350/169, 170, 436, 437, 350/286; 356/326, 327, 330

[56] References Cited

U.S. PATENT DOCUMENTS

| | | | |
|---|---|---|---|
| 2,090,398 | 8/1937 | Hoyt | 350/170 |
| 2,098,767 | 11/1937 | Thomas | 350/170 |
| 4,637,717 | 1/1987 | Brudnoy | 350/169 |
| 4,772,094 | 9/1988 | Sheimann | 350/133 |

FOREIGN PATENT DOCUMENTS 435222  9/1935  United Kingdom ............... 350/170

Primary Examiner—Eugene R. Laroche
Assistant Examiner—Ronald M. Kachmarik
Attorney, Agent, or Firm—Roger N. Coe

[57] ABSTRACT

An optical transmission spectrometer for transmission measurements of absorbing and scattering samples includes light sources mounted parallel to each other in a holder. The beams of light eminating from the light sources are directed through a beam-combiner. The beam-combiner includes a first refractive surface at an angle of incidence of 45°. The first refractive surface refracts light toward a common axis. The beam-combiner includes a second refractive surface parallel to the first refractive surface for refracting the beam of light along a common axis parallel to the original direction of the beam of light. The beam-combiner can include additional refractive surfaces for other beams of light to combine the beams of light into a primary beam. The includes a collimating tube extending along the common axis for baffling stray light and directing the primary beam through a sample. A second collimating tube is provided on the side of the sample opposite the first collimating tube for baffling stray light passing through the sample. The second collimating tube directs the primary beam to a detector package mounted in a holder, where the detector viewing area of the sample is limited to that of the primary beam.

7 Claims, 2 Drawing Sheets

OPTICAL TRANSMISSION SPECTROMETER

BACKGROUND OF THE INVENTION

A. Field of the Invention

The device of the present invention generally relates to a new and improved optical transmission spectrometer for transmission measurements of scattering and absorbing samples, and more particularly, to a new and improved light beam-combiner for an optical transmission spectrometer, and a method for combining light beams from parallel sources in an optical transmission spectrometer.

B. Description of the Prior Art

Optical transmission spectrometers are commonly used to read the amount of constituents in samples such as blood samples. Typically, these instruments cannot be used to make transmission measurements of scattering sample medium. Optical transmission spectrometers can include two sources of light arranged at 90° to each other. The two light sources are at different wavelengths. Performing measurements requires combining the two independent beams of light.

The typical prior art optical transmission spectrometer includes an optic known as a beamsplitter for combining the beams of light. The optic is a translucent plate mounted in the spectrometer at 45° to the two incoming beams of light. In this position, the beamsplitter combines the first and second beams into a common beam directing this common beam through the specimen and onto a detector. Careful assembly of the spectrometer is required since the optic must be mounted at exactly 45° to the two beams of light. Thus, precise mounting of the light sources and the optic relative to the light sources is required. A small deviation in the mounting of any of these elements results in an inoperative or inaccurate spectrometer. The optic imposes a restriction on the spectrometer since the optic can only combine two light sources, thus limiting the utility of the spectrometer in the number of tests that can be performed.

It is desirable to provide an optical transmission spectrometer that can use multiple light sources of different wavelengths allowing the instrument to conduct multiple tests on a single specimen. It is also desirable to provide a spectrometer that is small in size and uses parallel optical axes for the light sources rather than light source axes that are perpendicular to each other as in the prior art.

SUMMARY OF THE INVENTION

An object of the present invention is to provide a new and improved optical transmission spectrometer for measuring constituents in a sample.

Another object of the present invention is to provide a new and improved optical transmission spectrometer capable of conducting multiple tests on a single specimen.

A further object of the present invention is to provide a new and improved optical transmission spectrometer including a plurality of parallel optical axes for the light sources each producing light at a different wavelength.

A still further object of the present invention is to provide a new and improved optical transmission spectrometer including a plurality of light sources and an optic for combining the beams of light from the light sources along a common axis parallel to the axis of the original beams.

Another object of the present invention is to provide a new and improved optical transmission spectrometer that can perform transmission measurements on scattering and absorbing related samples Briefly, the present invention is directed to a new and improved instrument, commonly referred to as an optical transmission spectrometer, for measuring the absorption and scattering of light passing through a specimen, and thereby conducting one or more tests to measure constituents in the specimen.

The spectrometer of the present invention includes a plurality of sources of light mounted parallel to each other. An optic or light beam-combiner is mounted in the spectrometer adjacent the sources of light. The beam-combiner includes a first refractive surface aligned at an angle of incidence of 45°, and a second refractive surface parallel to the first refractive surface. The first refractive surface refracts a first light beam toward a common or central axis of the optic The second refractive surface refracts the beam along the common axis and parallel to its original path. Additional refractive surfaces perpendicular to the first and second refractive surfaces may be included on the beam-combiner for refracting additional beams of light.

The beam-combiner is fabricated prior to mounting in the spectrometer. Since the critical dimensions and angles on the optic are fabricated prior to assembly of the spectrometer, the necessity for precise alignment of the beam-combiner with the light sources during assembly of the spectrometer is minimized.

Since light passing through the optic is scattered and the sources of light inherently produce stray light, a first collimating tube is mounted in the spectrometer along the common axis and adjacent the beam-combiner to baffle this stray light and to transmit a primary beam to a sample area. A second collimating tube is mounted on the opposite side of the sample area from the first collimating tube to define the detector viewing area of the sample, and baffle stray light scattered by the sample and to transmit a primary beam to a detector mounted in the spectrometer. The detector measures the transmission of the primary beam and provides a reading in accordance with the particular test for which the spectrometer is being used.

BRIEF DESCRIPTION OF THE DRAWINGS

The above and other objects and advantages and novel features of the present invention will become apparent from the following detailed description of a preferred embodiment of the invention illustrated in the accompanying drawings wherein.

DESCRIPTION OF THE PREFERRED EMBODIMENT

Figure 1:
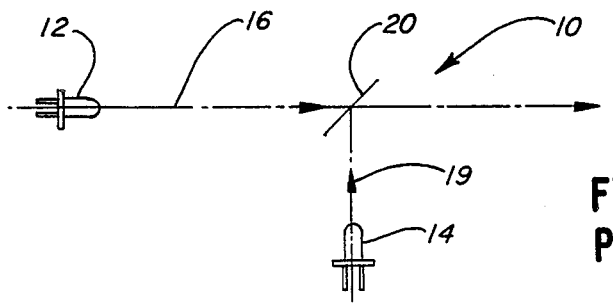
FIG. 1 is a schematic illustration of a prior art beam-combiner or beamsplitter for combining the light beams of two sources of light oriented perpendicular to each other.

Referring to the drawings and initially to FIG. 1, there is illustrated a prior art beamsplitter generally designated by the reference numeral 10. The prior art beamsplitter 10 is the traditional way to combine or split two independent, perpendicular beams of light from a first light source 12 and a second light source 14. A light beam 16 from the first light source 12 is combined with a second light beam 18 from the second light source 14 by an optic 20 to produce a combined or single beam 22.

The optic 20 is a clear material that must be aligned precisely at 45° to the incoming light beam 16 and the incoming light beam 18. The 90° orientation of the light beams 16 and 18 and the light sources 12 and 14 requires a particular housing which is bulky and too large for a portable instrument.

The 45° alignment of the optic 20 to beams 16 and 18 necessitates each individual instrument to be assembled carefully and checked for proper alignment. Even after proper alignment of the optic 20, the instrument can become misaligned during usage requiring recalibration at the factory or point of manufacture.

Due to the alignment of optic 20 and the fact that it can be manufactured with only two surfaces, the number of light beams that can be combined using the optic 20 is limited. By limiting the number of light beams to two, the number of tests that each instrument can conduct is also limited.

Figure 2:
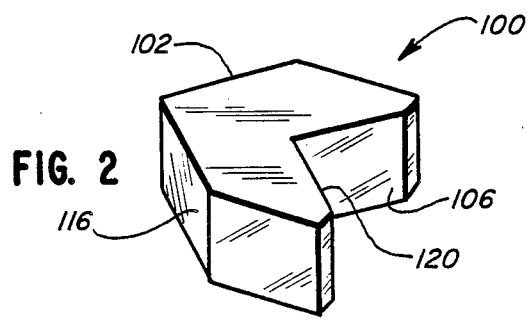
FIG. 2 is a perspective view of a beamcombiner constructed in accordance with the principles of the present invention.
Figure 3:
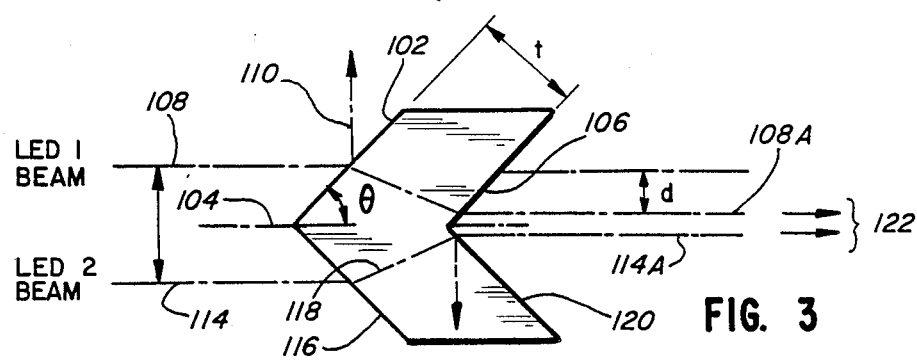
FIG. 3 is a schematic illustration of the paths of light beams through the beam-combiner of the present invention.

Referring now to FIGS. 2 and 3, optic 100 is capable of combining multiple light beams into a common or primary beam, and allows the sources of the light beams to be parallel to each other and closely aligned. This arrangement allows an instrument including the optic 100 to be made smaller and more portable.

The optic 100 is fabricated from translucent material such as acrylic or polycarbonate with a first refractive or first surface to air interface 102. The first surface 102 is at an angle of incidence $\theta$ which is 45° measured relative to a central or common axis 104 (FIG. 2). A second refractive surface or second surface to air interface 106 is fabricated on the optic 100 and oriented parallel to the first refractive surface 102. The second refractive surface 106 is spaced from the first refractive surface 102 by the thickness t of the optic 100 measured perpendicularly to the first refractive surface 102 and the second refractive surface 106.

As a first source light beam 108 hits the first refractive surface 102, part of that first source light beam 108 is reflected at a 45° angle to the first refractive surface 102 to define a first reflected beam 110. Another component of the first source light beam 108 is refracted forming a first refracted light beam 112 passing through the optic 100 and refracted toward the central or common axis 104.

As the first refracted light beam 112 hits the second refractive surface 106, it is refracted parallel to the original source beam 108. The first refracted source beam exiting the optic 100 is designated by the reference numeral 108A (FIG. 3). The first refracted source beam 108A is displaced a distance d from the original source beam 108 by the optic 100.

Figure 4:
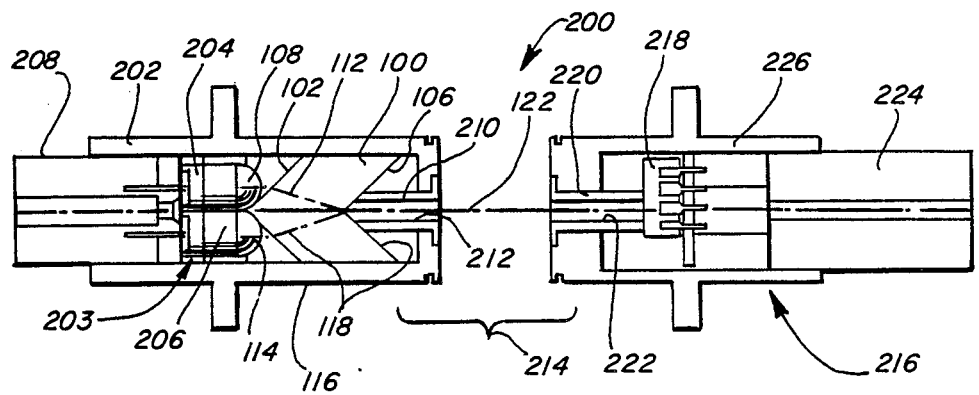
FIG. 4 is a vertical cross-sectional, reduced view of a optical transmission spectrometer including the beam-combiner of the present invention.

In a similar fashion, a second source light beam 114 hits a third refractive surface 116 on the optic 100 forming a second refracted beam 118 that passes through the optic 100 and is refracted toward the common axis 104. The third refractive surface 116 is perpendicular to the first refractive surface 102 and is at a 45° angle to the common axis 104. The second refracted light beam 118 after passing through the optic 100, hits a fourth refractive surface 120. The fourth refractive surface 120 is parallel to the third refractive surface 116 and spaced from it by a distance equal to the thickness t. The fourth refractive surface 120 is perpendicular to the second refractive surface 106. The second refracted light beam 118 is refracted along the common axis 104 by the fourth refractive surface 120 forming a second refracted source beam 114A which is parallel to the second source light beam 114 and is displaced a distance d from the second source light beam 114. The first refracted source light beam 108A and the second refracted source light beam 114A are spaced a sufficiently small distance apart such that they are in effect a single or primary beam of light extending along the common axis 104. This combined beam is designated by the reference numeral 122 (FIGS. 3 and 4).

The displacement d of the light beams 108 and 114 is a function of the thickness t of the optic 100. This displacement d may be calculated in accordance with the following equation:

$$d = t\, SIN\theta \left[ 1 - \sqrt{\frac{1 - SIN^2\theta}{N^2 - SIN^2\theta}} \right]$$

Where N is the index of refraction and $\theta$ is the angle of incidence of the source light on the optic 100. For example, if the thickness of the optic 100 is 0.34 inch, which is standard for stock acrylic glass, and the index of reflection N of the acrylic glass is 1.491, and the angle of incidence is 45°; using the above formula the displacement d is calculated to be 0.1125 inch.

The optic 100 can be used in transmission or reflective instruments. An example of a transmission instrument is the optic transmission spectrometer generally designated by the reference numeral 200 and illustrated in FIG. 4. The spectrometer 200 can be used for both absorbing and scattering samples and has multiwavelength capability allowing it to conduct multiple tests on a single specimen.

In the spectrometer 200, the optic 100 is mounted in an optic and light housing 202. The housing 202 and thus the optic 100 can be of any configuration such as square, rectangular or tubular. A preferred embodiment of the present invention is a tubular housing 202 and optic 100. Since the configuration of the optic 100 and the housing 202 are substantially the same, assembly of the spectrometer 200 merely requires sliding the prefabricated optic 100 into the housing 202 and rotating it to the correct position relative to the light source bundle 203. If there is misalignment of the light source bundle 203 relative to the optic 100, this misalignment is easily corrected by rotation of a light source holder 208 which mounts the light source bundle 203 in the housing 202. In contrast, in the prior art beamsplitter 10, precise location of the light sources 12 and 14 and the angle of the optic 20 are critical and not easily realigned after misalignment.

Easy correction of misalignment allows the optic 100 to be manufactured separately from spectrometer 200 and allows automated assembly since the alignment of the optic 100 is not as critical as in prior art beamsplitter. The light source bundle 203 includes several light sources such as a first light source 204 and a second light source 206 mounted in the housing 202 adjacent the optic 100. The light sources in the bundle 203 share a common optical axis eliminating the need for independent detectors. Although two light sources 204 and 206 are illustrated for ease of understanding, at least eight light sources can be included in light source bundle 203. For each light source, there are a pair of parallel reflective surfaces on the optic 100.

Upon energization, the first light source 204 generates and transmits the first source light beam 108. The second light source 206, upon energization, generates and transmits the second source light beam 114. Preferably, the first light source 204 and the second light source 206 are light emitting diodes (LED) of different wavelengths with highly collimated outputs. High collimation results in high optical throughput and lower stray light. LEDs of this type have flat reference surfaces providing accurate mechanical alignment. In a preferred embodiment, Siemens PN-GL 500 and IRL 500 LEDs are used.

The bundle of light sources including the first light source 204 and the second light source 206 are held by the light source holder 208 which is secured in the optic and light housing 202.

Upon energization of the first light source 204 and the second light source 206, the first source light beam 108 and the second source light beam 114 are refracted by the optic 100. The resultant combined primary beam 122 passes into and through a first collimating tube 210. The first collimating tube 210 has baffles on the interior surface in the form of threads 212. The threads or baffles 212 function to baffle stray or scattered light and allow transmission of only the primary beam 122 along collimating tube 210. The primary beam 122 is transmitted to a read or sample area 214.

Typically, a sample holder or reaction vessel for performing analytical assays is positioned in the read area 214. The primary beam 122 passes through the sample in the sample holder. A portion of the primary beam 122 is absorbed by the different materials and reagents in the sample while other portions of the primary beam 122 are reflected or scattered resulting in stray light.

After passing through the sample or specimen (not shown), the primary beam 122 is detected by a detector assembly generally designated by the reference numeral 216. The detector assembly 216 includes a detector amplifier package 218 that detects and measures the primary beam 122 after passage through the specimen. The detector amplifier package 218 is held by a detector holder 224, and the entire detector amplifier package 218 is housed in a housing 226.

The primary beam 122, after passing through the sample (not shown), is transmitted to the detector amplifier assembly 218 by a second collimating tube 220. The second collimating tube 220 includes baffles in the form of internal threads 222 which serve to baffle stray or scattered light resulting from scattering of the primary beam 122 as it passes through the sample being measured. The second collimating tube 220 serves to direct or transmit the primary beam 122 to the detector amplifier assembly 218. The second collimating tube 220 also apertures the detector in the detector amplifier assembly 218 at the proper distance from the sample defining the detector viewing area to that of the primary beam 122.

The spectrometer 200 employing the optic 100 can measure samples of both absorbing and scattering medium. The absorbing sample measurement measures the light absorbed by a colored liquid such as a colored sample in the read head 214. Typically, color is an indication of a constituent of the sample; for example, color in a blood sample would indicate the level of hemoglobin.

The spectrometer 200 also measures scattering sample medium. For example, after reagents that are mixed in a blood sample have dissipated, there are latex beads remaining in the sample. These remaining beads tend to scatter light in primary beam 122. The reading taken by the detector amplifier assembly 218 in this condition of the sample is a scattering measurement. The amount of scattering is a measurement of the amount of reaction that took place in the blood sample and how much hemoglobin $A_{1c}$ there is in the sample. Thus, a scattering measurement not normally obtainable in prior art spectrometers can be obtained.

Figure 5:
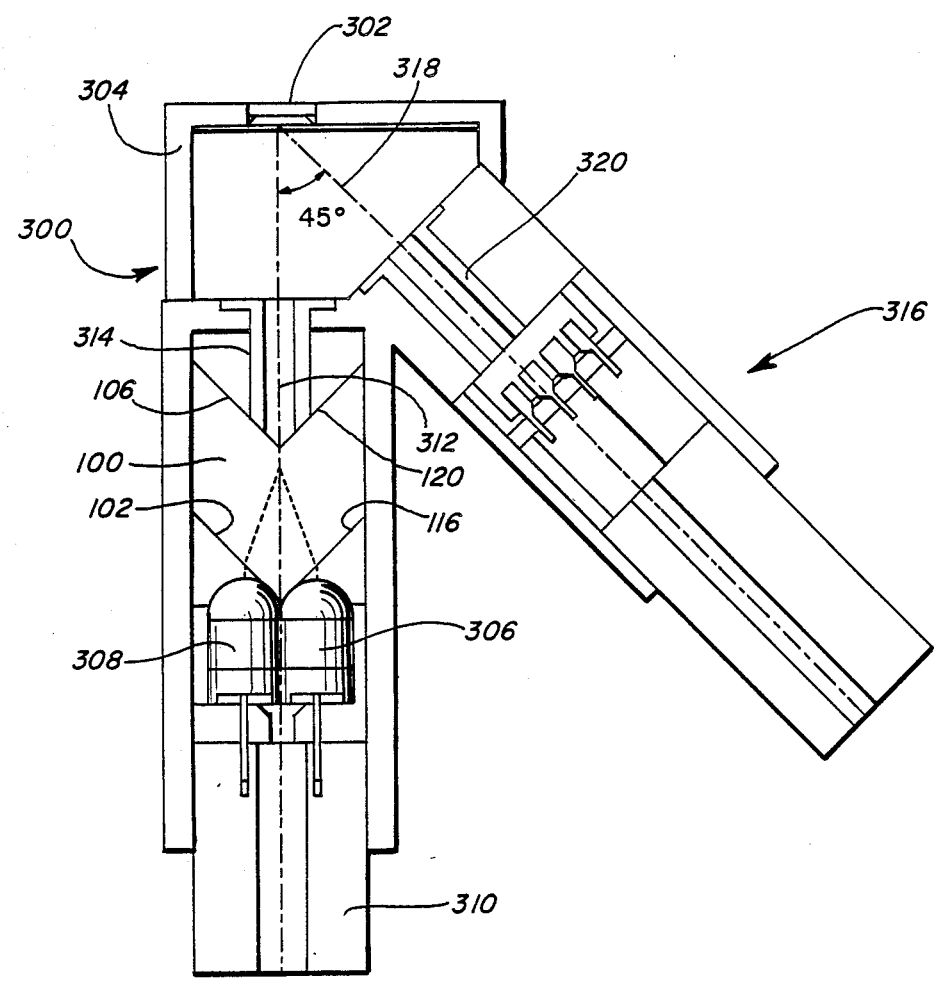
FIG. 5 is a cross-sectional, reduced plan view of a reflectance readhead including the beam-combiner of the present invention.

An example of a reflective instrument utilizing the optic 100 of the present invention is illustrated in FIG. 5. The reflective instrument is a reflectance readhead generally designated by the reference numeral 300. The reflectance readhead 300 is typically used to perform diffuse reflectance measurements on samples positioned adjacent a sample area aperture 302 defined in the housing 304 of the reflectance readhead 300.

Typically, a common readhead geometry with multi-wavelength capability for diffuse reflectance is 45°/0°. In this configuration a sample is illuminated at 45° with respect to the sample, and diffuse light is detected at 0°. Several illumination axes must be located radially around the 0° axis for the different light sources for each wavelength. By using the optic 100 of the present invention, only one optical illumination axis is required. Consequently, space and cost requirements are reduced since only two optical axes are required, and all light sources are located in the same area. In addition, the readhead illumination axis can be located on the 0° axis, thus improving optical performance by illuminating normal to the sample surface.

Light emitting diodes are commonly used as light sources in optical readheads that perform diffuse reflectance measurements. Each wavelength to be measured requires two light emitting diodes on independent optical axes where the light from both light emitting diodes illuminates the sample to be measured. By using the optic 100, one primary illumination optical axis along with two or more light emitting diodes at different wavelengths may be used in the reflectance readhead 300. This can be accomplished since the optic 100 combines several beams of light into one primary optical axis.

For example, the reflectance readhead 300 illustrated in FIG. 5 includes a first light source 306 and a second light source 308 that are held in a bundle by a light source holder 310. As discussed with the spectrometer 200, the light source bundle 310 may include more than the two light sources 306 and 308. Up to at least eight light sources mounted in a circular pattern in the housing 302 may be provided. For ease of illustration, however, only the two light sources 306 and 308 are illustrated.

The light sources 306 and 308 provide two different wavelengths and are mounted side- by-side. For each light source 306 and 308, a corresponding pair of refractive surfaces such as surfaces 102 and 106 of optic 100 are provided. The outputs of the light sources 306 and 308 pass through the optic 100 which displaces the outputs into a common center axis or beam 312. The combined beam 312 passes through a first collimating tube 314 which functions to block stray light from reaching a sample positioned adjacent the sample area aperture 302. The collimating tube 314 also defines the proper sample illumination area.

Diffuse light reflected from the sample is then detected by a detector amplifier generally designed by the reference numeral 316. Diffuse light 318 passes through a second collimating tube 320 which defines the detector viewing area and prevents stray light reflecting off the wall of the housing 304 surrounding the sample area aperture 302 from reaching the detector amplifier 316.

The optic 100, the spectrometer 200, and the reflectance readhead 300 each uses two or more light sources of different wavelengths which share a common optical axis thereby eliminating the need for more than one independent detector. In addition, the optical design of the optic 100, the spectrometer 200 and the reflectance readhead 300 eliminate stray or noncollimated light generated by the light sources and associated optics. Moreover, the optical design of the present invention requires no optical alignment during manufacturing.

What is claimed is:

1. An optical transmission spectrometer for absorbing and scattering sample readings, comprising:
    a plurality of light sources for producing light, the absorption of which in a sample is to be measured by the spectrometer;
    a holder for said plurality of light sources;
    a light beam-combiner for combining beams of light from said light sources by refraction into a primary beam of light, said light beam combiner including first and second parallel refractive surfaces for refracting light from said light sources into said primary beam;
    a first collimating device adjacent said light beam-combiner for baffling stray light passing from the said light beam-combiner and the light source;
    a mounting assembly for mounting a sample in the optical transmission spectrometer adjacent said first collimating device; and
    a detection assembly for detecting absorption of light passing through a sample in said mounting assembly.

2. The optical transmission spectrometer set forth in claim 1 wherein said light beam combiner includes a third refractive surface substantially perpendicular to said first refractive surface and a fourth refractive surface parallel to said third refractive surface, said third refractive surface and said fourth refractive surface refracting light from said light sources into said primary beam.

3. The optical transmission spectrometer set forth in claim 2 wherein each of said first refractive surface, said second refractive surface, said third refractive surface and said fourth refractive surface includes an angle of incidence of 45°.

4. The optical transmission spectrometer set forth in claim 1 further comprising a second collimating device mounted between said detection assembly and said mounting assembly for baffling stray light passing from a sample, and defining the detector viewing area to that of the primary beam passing through the sample area.

5. The optical transmission spectrometer set forth in claim 1 wherein the amount a beam of light is displaced upon passing through said beam-combiner can be calculated using the formula $$d = t\, \text{SIN}\theta \left[ 1 - \sqrt{\frac{1 - \text{SIN}^2\theta}{N^2 - \text{SIN}^2\theta}} \right]$$

where d is the amount of displacement, t is the thickness of the beam-combiner, N is the index of refraction of the beam-combiner and $\theta$ is the angle of incidence.

6. The optical transmission spectrometer set forth in claim 1 wherein said plurality of light sources includes two light emitting diodes of different wavelengths.

7. The optical transmission spectrometer set forth in claim 1 wherein said first collimating device is an internally threaded tube wherein threads on the interior of the tube baffle stray light.

* * * * *